US00PP35018P2

(12) United States Plant Patent
Mathey

(10) Patent No.: US PP35,018 P2
(45) Date of Patent: Mar. 7, 2023

(54) ***CHAENOMELES* PLANT NAMED 'SMNCSDW'**

(50) Latin Name: *Chaenomeles speciosa*
Varietal Denomination: SMNCSDW

(71) Applicant: Megan M. Mathey, Holland, MI (US)

(72) Inventor: Megan M. Mathey, Holland, MI (US)

(73) Assignee: SPRING MEADOW NURSERY INC., Grand Haven, MI (US)

( * ) Notice: Subject to any disclaimer, the term of this patent is extended or adjusted under 35 U.S.C. 154(b) by 0 days.

(21) Appl. No.: 17/952,972

(22) Filed: Sep. 26, 2022

(51) Int. Cl.
*A01H 5/00* (2018.01)
*A01H 6/74* (2018.01)

(52) U.S. Cl.
USPC ..... Plt./226

(58) Field of Classification Search
USPC ..... Plt./226
See application file for complete search history.

*Primary Examiner* — Karen M Redden
(74) *Attorney, Agent, or Firm* — C. Anne Whealy

(57) ABSTRACT

A new and distinct cultivar of *Chaenomeles* plant named 'SMNCSDW', characterized by its upright to outwardly sprawling plant habit; moderately vigorous growth habit and moderate to rapid growth rate; dark green-colored leaves; freely and continuously flowering from the spring into the autumn; double-type light yellow green-colored flowers that become pure white in color with development; and good garden performance.

2 Drawing Sheets

Figure 1:
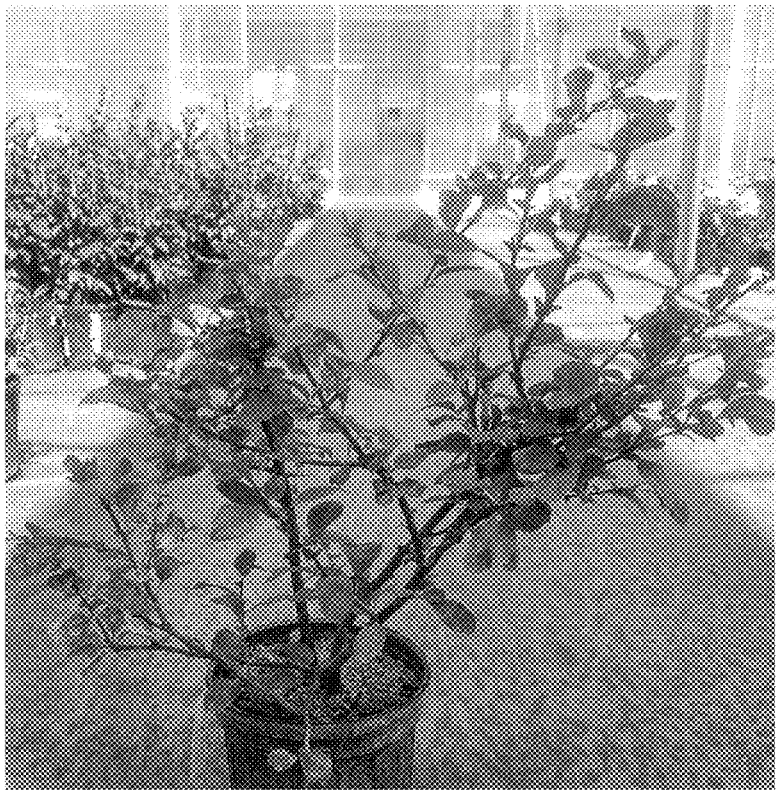

Botanical designation: *Chaenomeles speciosa.*
Cultivar denomination: 'SMNCSDW'.

BACKGROUND OF THE INVENTION

The present Invention relates to a new and distinct cultivar of *Chaenomeles* plant, botanically known as *Chaenomeles speciosa*, commonly referred to as Flowering Quince, and hereinafter referred to by the name 'SMNCSDW'.

The new *Chaenomeles* plant is a product of a planned breeding program conducted by the Inventor in Grand Haven, Mich. The objective of the breeding program was to develop new uniform *Chaenomeles* varieties with durable and healthy foliage and attractive white-colored flowers.

The new *Chaenomeles* plant originated from an open-pollination in 2014 of an unidentified proprietary *Chaenomeles speciosa* selection, not patented, as the female, or seed, parent with an unknown proprietary *Chaenomeles speciosa* selection as the male, or pollen, parent. The new *Chaenomeles* plant was discovered and selected by the Inventor as a single flowering plant within the progeny of the stated open-pollination in a controlled outdoor nursery environment in Grand Haven, Mich. in 2016.

Asexual reproduction of the new *Chaenomeles* plant by softwood cuttings in Grand Haven, Mich. since 2016 has shown that the unique features of this new *Chaenomeles* plant are stable and reproduced true to type in successive generations of asexual reproduction.

SUMMARY OF THE INVENTION

Plants of the new *Chaenomeles* have not been observed under all possible combinations of environmental conditions and cultural practices. The phenotype may vary somewhat with variations in environmental conditions such as temperature and light intensity, without however, any variance in genotype.

The following traits have been repeatedly observed and are determined to be the unique characteristics of 'SMNCSDW'. These characteristics in combination distinguish 'SMNCSDW' as a new and distinct *Chaenomeles* plant:

1. Upright to outwardly sprawling plant habit.
2. Moderately vigorous growth habit and moderate to rapid growth rate.
3. Dark green-colored leaves.
4. Freely and continuously flowering from the spring into the autumn.
5. Double-type light yellow green-colored flowers that become pure white in color with development.
6. Good garden performance.

Plants of the new *Chaenomeles* differ from plants of the female parent selection in the following characteristics:

1. Flowers of plants of the new *Chaenomeles* are double-types whereas flowers of plants of the female parent selection are single-types.
2. Fully expanded flowers of plants of the new *Chaenomeles* are white in color whereas fully expanded flowers of plants of the female parent selection are reddish pink in color.

Plants of the new *Chaenomeles* can also be compared to plants of *Chaenomeles speciosa* 'Nivalis', not patented. In side-by-side comparisons, plants of the new *Chaenomeles* differ from plants of 'Nivalis' in the following characteristics:

1. Plants of the new *Chaenomeles* are smaller than plants of 'Nivalis'.
2. Stems of plants of the new *Chaenomeles* do not have thorns whereas stems of plants of 'Nivalis' have thorns.
3. Flowers of plants of the new *Chaenomeles* are double-types whereas flowers of plants of 'Nivalis' are single-types.

BRIEF DESCRIPTION OF THE PHOTOGRAPHS

The accompanying colored photographic sheet illustrates the overall appearance of the new *Chaenomeles* plant showing the colors as true as it is reasonably possible to obtain in colored reproductions of this type. Colors in the photograph may differ slightly from the color values cited in the detailed botanical description which accurately describe the colors of the new *Chaenomeles* plant.

The photograph on the first sheet (FIG. 1) is a side perspective view of a typical plant of 'SMNCSDW' grown in a container.

Figure 2:
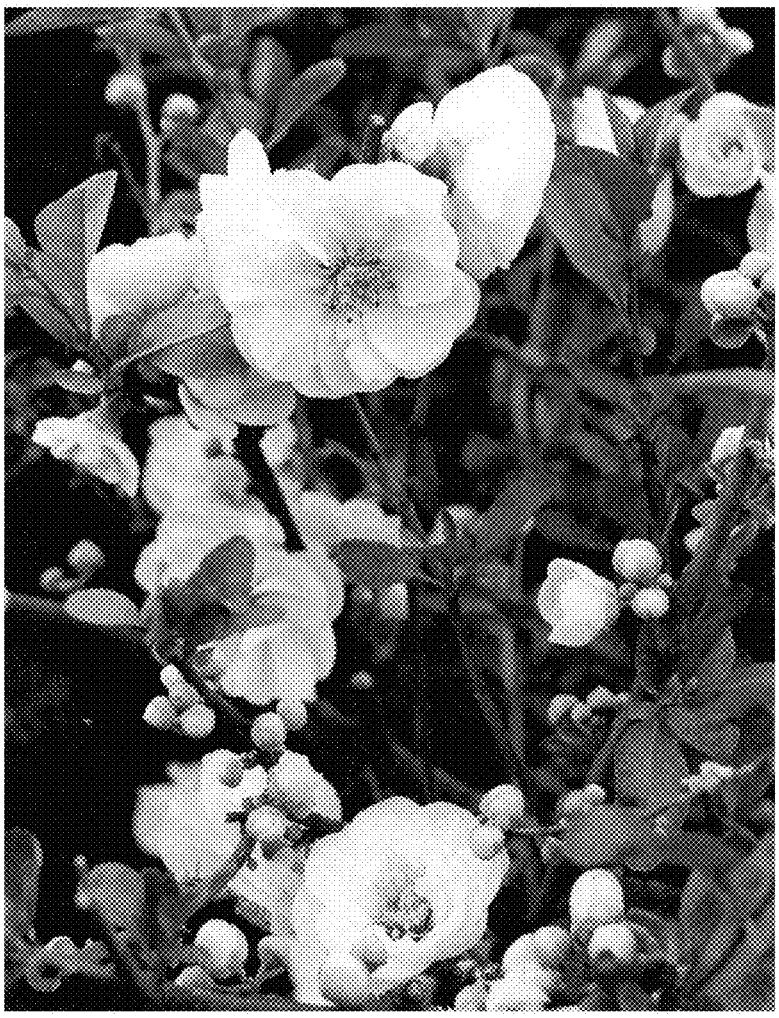

The photograph on the second sheet (FIG. 2) is a close-up view of a typical flowering plant of 'SMNCSDW'.

DETAILED BOTANICAL DESCRIPTION

The aforementioned photographs, following observations and measurements describe plants grown during the spring in three-gallon containers in a polyethylene-covered greenhouse in Grand Haven, Mich. and under typical *Chaenomeles* production practices. Plants were three years old when the photographs and the description were taken. During the production of the plants, day temperatures ranged from 18° C. to 27° C. and night temperatures ranged from 5° C. to 10° C. In the following description, color references are made to The Royal Horticultural Society Colour Chart, 2015 Edition, except where general terms of ordinary dictionary significance are used.

Botanical classification: *Chaenomeles speciosa* 'SMNCSDW'.

Parentage:

*Female, or seed, parent*.—Unidentified proprietary selection of *Chaenomeles speciosa*, not patented.

*Male, or pollen, parent*.—Unknown proprietary selection of *Chaenomeles speciosa*, not patented.

Propagation:

*Type*.—By softwood cuttings.

*Time to initiate roots, summer*.—About four weeks at temperatures about 18° C. to 27° C.

*Time to produce a rooted young plant, summer*.—About eight weeks at temperatures about 18° C. to 27° C.

*Root description*.—Fine to medium in thickness, fibrous; typically brown and creamy white in color, actual color of the roots is dependent on substrate composition, water quality, fertilizers, substrate temperature and age of roots.

*Rooting habit*.—Freely branching; medium density.

Plant description:

*Plant and growth habit*.—Perennial shrub; upright to outwardly sprawling plant form; pruning will result in a more mounded and uniform habit; moderately vigorous growth habit and moderate to rapid growth rate.

*Plant height*.—About 40 cm.

*Plant width* (*spread*).—About 45 cm.

*Lateral branches*.—Quantity per plant: About ten; pruning will enhance lateral branch development. Length: About 35 cm. Diameter: About 5 mm. Internode length: About 2 cm. Texture: Smooth, glabrous; thorn development has not been observed on plants of the new *Chaenomeles*. Aspect: About 45° to 80° from vertical. Strength: Strong. Color, developing: Close to 144B to 144C. Color, developed: Close to N199B.

Leaf description:

*Arrangement*.—Alternate; single.

*Length*.—About 5 cm.

*Width*.—About 3 cm.

*Shape*.—Elliptic.

*Apex*.—Acute.

*Base*.—Attenuate.

*Margin*.—Serrulate.

*Texture, upper surface*.—Smooth, glabrous; somewhat coriaceous.

*Texture, lower surface*.—Smooth, glabrous with prominent midvein; somewhat coriaceous.

*Venation pattern*.—Pinnate.

*Color*.—Developing leaves, upper surface: Close to 144B slightly tinged with close to N167B. Developing leaves, lower surface: Close to 147C. Fully expanded leaves, upper surface: Close to 147A; venation, close to 144C. Fully expanded leaves, lower surface: Close to 147B; venation, close to 144C.

*Petioles*.—Length: About 1 cm. Diameter: About 1 mm. Strength: Moderately strong. Texture, upper and lower surfaces: Smooth, glabrous. Color, upper and lower surfaces: Close to 144C.

*Stipules*.—Arrangement and appearance: Two, adnate to the petiole, leafy in appearance. Length: About 1 cm. Width: About 7 mm. Shape: Roughly reniform. Apex: Obtuse. Base: Cordate. Margin: Serrulate. Texture, upper and lower surfaces: Smooth, glabrous; somewhat coriaceous. Venation pattern: Pinnate. Color: Developing stipules, upper surface: Close to 144B slightly tinged with close to N167B. Developing stipules, lower surface: Close to 147C. Fully expanded stipules, upper surface: Close to 147A. Fully expanded stipules, lower surface: Close to 147B.

Flower description:

*Flower type, arrangement and quantity*.—Symmetrical rotate double-type flowers; flowers axillary and either solitary or in clusters of two to four; about 15 to 30 flowers and flower buds per lateral stem and about 200 flowers per plant; flowers face upright to outwardly; flowers not persistent.

*Flowering season*.—Plants of the new *Chaenomeles* flower from the spring into the autumn in an outdoor nursery in Grand Haven, Mich.

*Flower diameter*.—About 5 cm to 6 cm.

*Flower depth* (*height*).—About 1.5 cm.

*Fragrance*.—None detected.

*Flower buds*.—Length: About 1 cm to 1.5 cm. Diameter: About 8 mm. Shape: Ovoid. Texture: Smooth, glabrous. Color: Close to 143C.

*Petals*.—Quantity and arrangement: About 20 to 25 per flower arranged in two whorls; petals are not fused. Length: About 2.25 cm. Width: About 2 cm. Shape: Nearly orbicular. Apex: Obtuse. Base: Attenuate. Margin: Slightly sinuate; ruffled in appearance. Texture, upper and lower surfaces: Smooth, glabrous; soft. Color: When opening, upper and lower surfaces: Close to 145D. Fully opened, upper and lower surfaces: Close to NN155A; venation, close to NN155A; color does not change with subsequent development.

*Petaloids*.—Quantity and arrangement: About two to four in a single whorl. Length: About 1.75 cm. Width: About 7.5 mm. Shape: Irregular to roughly oblong. Apex: Obtuse. Base: Acuminate. Margin: Crenate. Texture, upper and lower surfaces: Smooth, glabrous; soft. Color: When opening, upper and lower surfaces: Close to 145D. Fully opened, upper and lower surfaces: Close to NN155A; venation, close to NN155A; color does not change with subsequent development.

*Sepals*.—Quantity per flower: Typically six in a single whorl; fused at the base. Length: About 4 mm. Width: About 5 mm. Shape: Roughly rectangular. Apex: Retuse. Margin: Entire. Texture, upper and lower surfaces: Smooth, glabrous. Color, upper surface: Close to 144C. Color, lower surface: Close to 144B.

*Peduncles*.—Length: About 7.5 mm. Diameter: About 1.5 mm. Strength: Strong. Aspect: About 90° from stem axis. Texture: Smooth, glabrous. Color: Close to 144B.

*Reproductive organs*.—Stamens: Quantity per flower: About 100. Filament length: About 6 mm. Filament color: Close to NN155A. Anther length: About 1 mm to 2 mm. Anther shape: Rounded to globular. Anther color: Close to 14C. Pollen amount: If present, scarce. Pollen color: Close to 14C. Pistils: To date, pistil development has not been observed on plants of the new *Chaenomeles*.

*Fruits and seeds*.—To date, fruit and seed development have not been observed on plants of the new *Chaenomeles*.

Pathogen & pest tolerance: To date, plants of the new *Chaenomeles* have not been observed to be tolerant to pathogens and pests common to *Chaenomeles* plants.

Garden performance: Plants of the new *Chaenomeles* have been observed to have good garden performance and to tolerate temperatures ranging from −31° C. to 38° C.

It is claimed:

1. A new and distinct *Chaenomeles* plant named 'SMNCSDW' as illustrated and described.

* * * * *